US010420202B2

(12) United States Patent
Matsumoto et al.

(10) Patent No.: US 10,420,202 B2
(45) Date of Patent: Sep. 17, 2019

(54) ACCELERATOR CONTROL DEVICE, ACCELERATOR CONTROL METHOD, AND PARTICLE BEAM THERAPY DEVICE

(71) Applicants: Toshiba Energy Systems & Solutions Corporation, Kawasaki-shi (JP); National Institutes for Quantum and Radiological Science and Technology, Chiba-shi (JP)

(72) Inventors: Munemichi Matsumoto, Fuchu (JP); Takuji Furukawa, Chiba (JP); Kota Mizushima, Chiba (JP); Katsushi Hanawa, Kita (JP)

(73) Assignees: Toshiba Energy Systems & Solutions Corporation, Kawasaki-shi (JP); National Institutes for Quantum and Radiological Science and Technology, Chiba-shi (JP)

( * ) Notice: Subject to any disclaimer, the term of this patent is extended or adjusted under 35 U.S.C. 154(b) by 0 days.

(21) Appl. No.: 15/963,641

(22) Filed: Apr. 26, 2018

(65) Prior Publication Data
US 2018/0317311 A1    Nov. 1, 2018

(30) Foreign Application Priority Data
May 1, 2017   (JP) .................. 2017-091279

(51) Int. Cl.
*A61N 5/10*    (2006.01)
*H05H 7/02*    (2006.01)
*H05H 13/04*   (2006.01)

(52) U.S. Cl.
CPC .............. *H05H 7/02* (2013.01); *A61N 5/1048* (2013.01); *A61N 5/1077* (2013.01);
(Continued)

(58) Field of Classification Search
CPC .... H05H 7/02; H05H 13/04; H05H 2007/022; H05H 2007/025; H05H 2277/11;
(Continued)

(56) References Cited

U.S. PATENT DOCUMENTS 7,875,868 B2    1/2011  Moriyama et al.
2016/0330827 A1 11/2016 Sugahara et al.

FOREIGN PATENT DOCUMENTS

EP    2750484 A1    7/2014
JP    04-264400     9/1992
(Continued)

OTHER PUBLICATIONS

Mizushima, K., et al. "Reliable Beam-Intensity Control Technique at the Himac Synchrotron", Proceedings of the 1st International Beam Instrumentation Conference, Tsukuba, Japan, 2012, pp. 143-145.

*Primary Examiner* — Nicole M Ippolito
*Assistant Examiner* — Hanway Chang
(74) *Attorney, Agent, or Firm* — Oblon, McClelland, Maier & Neustadt, L.L.P.

(57) ABSTRACT

According to some embodiments, an accelerator control device has a high-frequency power controller and a timing controller. The high-frequency power controller supplies high frequency power for accelerating a charged particle beam to an accelerator. The timing controller controls an operation timing of a blocker that blocks the charged particle beam emitted from the accelerator based on a current value of the charged particle beam circulating in the accelerator.

15 Claims, 12 Drawing Sheets

(52) U.S. Cl.
CPC ..... *H05H 13/04* (2013.01); *A61N 2005/1074* (2013.01); *A61N 2005/1087* (2013.01); *A61N 2005/1095* (2013.01); *H05H 2007/022* (2013.01); *H05H 2007/025* (2013.01); *H05H 2277/11* (2013.01)

(58) Field of Classification Search
CPC ................ A61N 5/1048; A61N 5/1077; A61N 2005/1074; A61N 2005/1087; A61N 2005/1095
USPC ...... 250/492.1, 492.2, 492.3, 281, 282, 286, 250/288, 290, 291, 294
See application file for complete search history.

(56) References Cited

FOREIGN PATENT DOCUMENTS

| | | |
|---|---|---|
| JP | 2009-148473 | 7/2009 |
| JP | 2010-251106 | 11/2010 |
| JP | 2011-34823 | 2/2011 |
| JP | 4873563 | 2/2012 |
| JP | 2013-094313 | 5/2013 |
| SG | 189670 A1 | 5/2013 |

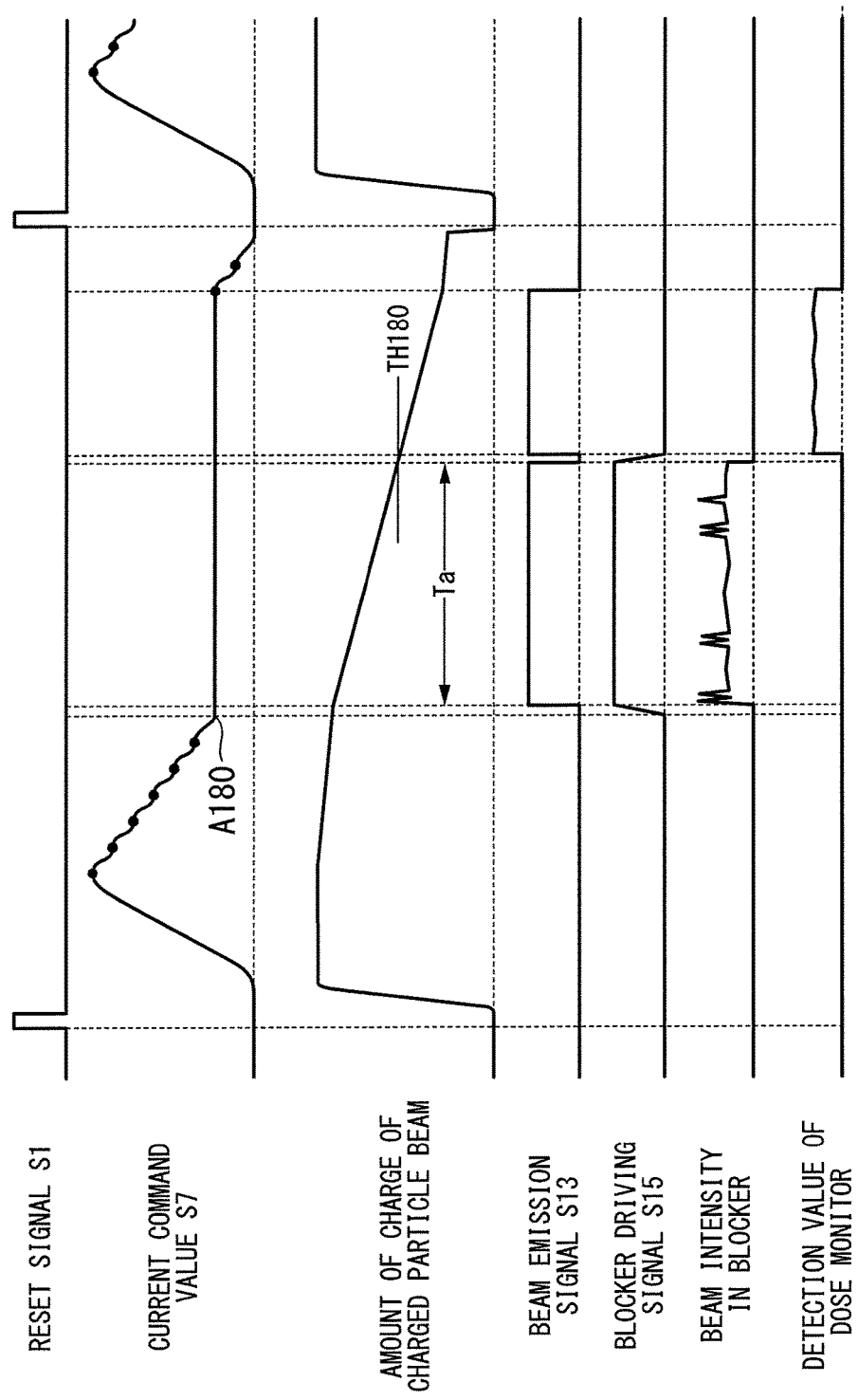

FIG. 6

|  | ENERGY NUMBER | BEAM CHARGE AMOUNT THRESHOLD VALUE |
|---|---|---|
| HIGH ENERGY | 1 | 100 |
|  | 2 | 100 |
|  | 3 | 100 |
|  | ... | 100 |
|  | n | 1.4 |
|  | ... | 1.3 |
|  | 198 | 1.2 |
|  | 199 | 1.1 |
| LOW ENERGY | 200 | 1 |

FIG. 7

| CONTENT OF PARAMETER | VALUE |
|---|---|
| BOUNDARY ENERGY NUMBER | 180 |
| BEAM CHARGE AMOUNT THRESHOLD VALUE 1 | 20 |
| BEAM CHARGE AMOUNT THRESHOLD VALUE 2 | 1 |

FIG. 8

| CONTENT OF PARAMETER | VALUE |
|---|---|
| BOUNDARY ENERGY NUMBER 1 | 150 |
| BOUNDARY ENERGY NUMBER 2 | 180 |
| BEAM CHARGE AMOUNT THRESHOLD VALUE 1 | 10 |
| BEAM CHARGE AMOUNT THRESHOLD VALUE 2 | 2 |
| BEAM CHARGE AMOUNT THRESHOLD VALUE 3 | 1 |

FIG. 12

| | ENERGY NUMBER | CHOPPER PULSE WIDTH |
|---|---|---|
| HIGH ENERGY | 1 | 40 |
| | 2 | 35 |
| | 3 | 30 |
| | ... | |
| | n | |
| | ... | |
| | 198 | 10 |
| | 199 | 10 |
| LOW ENERGY | 200 | 10 |

FIG. 13

| CONTENT OF PARAMETER | VALUE |
|---|---|
| BOUNDARY ENERGY NUMBER | 180 |
| CHOPPER PULSE WIDTH 1 | 30 |
| CHOPPER PULSE WIDTH 2 | 10 |

FIG. 14

| CONTENT OF PARAMETER | VALUE |
|---|---|
| BOUNDARY ENERGY NUMBER 1 | 100 |
| BOUNDARY ENERGY NUMBER 2 | 180 |
| CHOPPER PULSE WIDTH 1 | 30 |
| CHOPPER PULSE WIDTH 2 | 20 |
| CHOPPER PULSE WIDTH 3 | 10 |

| | ENERGY NUMBER | BEAM CURRENT THRESHOLD VALUE |
|---|---|---|
| HIGH ENERGY | 1 | 50 |
| | 2 | 50 |
| | 3 | 50 |
|  | ... | 50 |
| | n | 0.7 |
| | ... | 0.65 |
| | 198 | 0.3 |
| | 199 | 0.5 |
| LOW ENERGY | 200 | 0.5 |

| CONTENT OF PARAMETER | VALUE |
|---|---|
| BOUNDARY ENERGY NUMBER | 180 |
| BEAM CURRENT THRESHOLD VALUE 1 | 10 |
| BEAM CURRENT THRESHOLD VALUE 2 | 0.5 |

| CONTENT OF PARAMETER | VALUE |
|---|---|
| BOUNDARY ENERGY NUMBER 1 | 150 |
| BOUNDARY ENERGY NUMBER 2 | 180 |
| BEAM CURRENT THRESHOLD VALUE 1 | 5 |
| BEAM CURRENT THRESHOLD VALUE 2 | 1 |
| BEAM CURRENT THRESHOLD VALUE 3 | 0.25 |

ACCELERATOR CONTROL DEVICE, ACCELERATOR CONTROL METHOD, AND PARTICLE BEAM THERAPY DEVICE

CROSS-REFERENCE TO RELATED APPLICATIONS

This application is based upon and claims the benefit of priority from Japanese Patent Application No. 2017-091279, filed May 1, 2017; the entire contents of which are incorporated herein by reference.

FIELD

Embodiments described herein relate generally to an accelerator control device, an accelerator control method, and a particle beam therapy device.

BACKGROUND

Generally, in a particle beam therapy device, an accelerator for accelerating a charged particle beam to a desired energy is provided. In the accelerator, a high-frequency acceleration cavity including a plurality of electrodes is provided. The particle beam therapy device accelerates the charged particle beam to a desired energy by supplying high frequency power to the electrode provided in the high-frequency acceleration cavity and irradiates an affected part such as a tumor with the accelerated charged particle beam.

However, immediately after the charged particle beam accelerated to constant energy by the accelerator is emitted, a phenomenon called beam spikes in which intensity of the charged particle beam exceeds a target value may occur. The beam spikes easily occur particularly when a charged particle beam with low energy is emitted.

BRIEF DESCRIPTION OF THE DRAWINGS

FIG. 5 is a timing chart illustrating an example of control of the blocker 155 according to the first embodiment.

FIG. 6 is a diagram illustrating an example of a charge amount threshold value table 313 according to the first embodiment.

FIG. 7 is a diagram illustrating another example of the charge amount threshold value table 313 according to the first embodiment.

FIG. 8 is a diagram illustrating another example of a charge amount threshold value table 313 according to the first embodiment.

FIG. 12 is a diagram illustrating an example of a pulse width threshold value table 315 according to the second embodiment.

FIG. 13 is a diagram illustrating another example of the pulse width threshold value table 315 according to the second embodiment.

FIG. 14 is a diagram illustrating another example of the pulse width threshold value table 315 according to the second embodiment.

DETAILED DESCRIPTION

According to some embodiments, an accelerator control device has a high-frequency power controller and a timing controller. The high-frequency power controller supplies high frequency power for accelerating a charged particle beam to an accelerator. The timing controller controls an operation timing of a blocker that blocks the charged particle beam emitted from the accelerator based on a current value of the charged particle beam circulating in the accelerator.

Hereinafter, an accelerator control device, an accelerator control method, and a particle beam therapy device according to embodiments will be described with reference to the drawings. The accelerator control device of the embodiments can be applied not only to a particle beam therapy device but also to various devices using a charged particle beam. For example, the present invention can also be applied to an etching device for processing a target by radiating a charged particle beam.

First Embodiment

Figure 1:
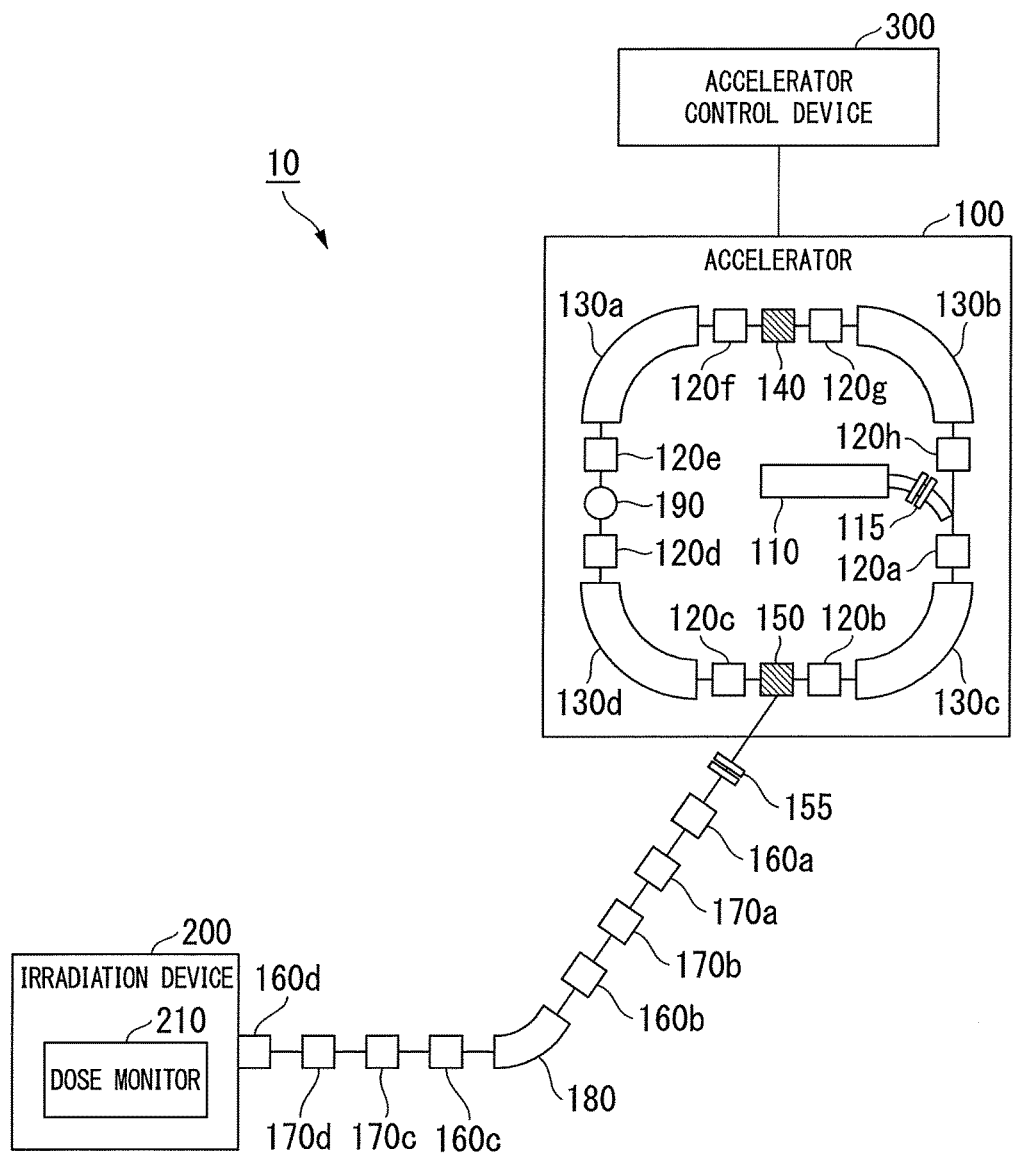
FIG. 1 is a block diagram illustrating an overall configuration of a particle beam therapy device 10 according to a first embodiment.

FIG. 1 is a block diagram illustrating an overall configuration of a particle beam therapy device 10 according to a first embodiment. The particle beam therapy device 10 is a device that accelerates a charged particle beam to a desired energy and irradiates an affected part such as a tumor with the accelerated charged particle beam. The particle beam therapy device 10 includes an accelerator 100, an irradiation device 200, and an accelerator control device 300.

The accelerator 100 includes an injector 110, a chopper 115, a plurality of quadrupole electromagnets 120a to 120h, a plurality of deflection electromagnets 130a to 130d, a high-frequency acceleration cavity 140, an emitter 150, and a current value detector 190.

The injector 110 causes the charged particle beam to be incident on a circulating trajectory in the accelerator 100. The chopper 115 is provided in order to adjust the amount of the charged particle beam that is incident on the accelerator 100. As the chopper 115, for example, a beam chopper that adjusts the incidence amount of the charged particle beam incident on the accelerator 100 by temporally switching and giving an electric or magnetic force for deflecting the charged particle beam may be used. The quadrupole electromagnets 120a to 120h are electromagnets that cause the charged particle beam to converge or diverge such that the charged particle beam stably circulates around the circulating trajectory.

The deflection electromagnets 130a to 130d are electromagnets that cause the charged particle beam to circulate in the accelerator 100 by deflecting the charged particle beam. The current value detector 190 detects the current value of the charged particle beam circulating in the accelerator 100.

A plurality of electrodes are provided in the high-frequency acceleration cavity 140. The charged particle beam is accelerated by applying a voltage to the plurality of electrodes provided in the high-frequency acceleration cavity 140. The emitter 150 emits some of the charged particle beam circulating around the circulating trajectory in the accelerator 100 toward the irradiation device 200 by applying a high frequency electric field to an emission electrode provided in the accelerator 100.

A blocker 155, a plurality of quadrupole electromagnets 160a to 160d, a plurality of correction electromagnets 170a to 170d, and a deflection electromagnet 180 are provided in a path from the accelerator 100 to the irradiation device 200. The blocker 155 is a shutter that blocks the charged particle beam emitted from the accelerator, but is not limited thereto as long as the blocker 155 can control the amount of beam reaching the irradiation device 200. For example, the blocker 155 may be a deflection electromagnet that guides the charged particle beam emitted from the accelerator to a path different from the path to the irradiation device 200, or an electrode that generates an electric field.

The quadrupole electromagnets 160a to 160d are electromagnets that cause the charged particle beam to converge or diverge such that the charged particle beam stably passes through the path from the accelerator 100 to the irradiation device 200 and the charged particle beam has a target beam diameter at an irradiation position. The deflection electromagnet 180 is an electromagnet for deflecting the charged particle beam and guiding the charged particle beam from the accelerator 100 to the irradiation device 200. The correction electromagnets 170a to 170d are electromagnets for correcting a trajectory of the charged particle beam from the accelerator 100 to the irradiation device 200.

The irradiation device 200 is a device that is installed in a treatment room and irradiates an affected part such as a tumor with the charged particle beam accelerated by the accelerator 100. The irradiation device 200 includes a dose monitor 210. The dose monitor 210 detects intensity of the charged particle beam with which the affected part is irradiated.

The accelerator control device 300 is a device that controls the accelerator 100 that accelerates the charged particle beam. Hereinafter, a detailed configuration of the accelerator control device 300 will be described.

Figure 2:
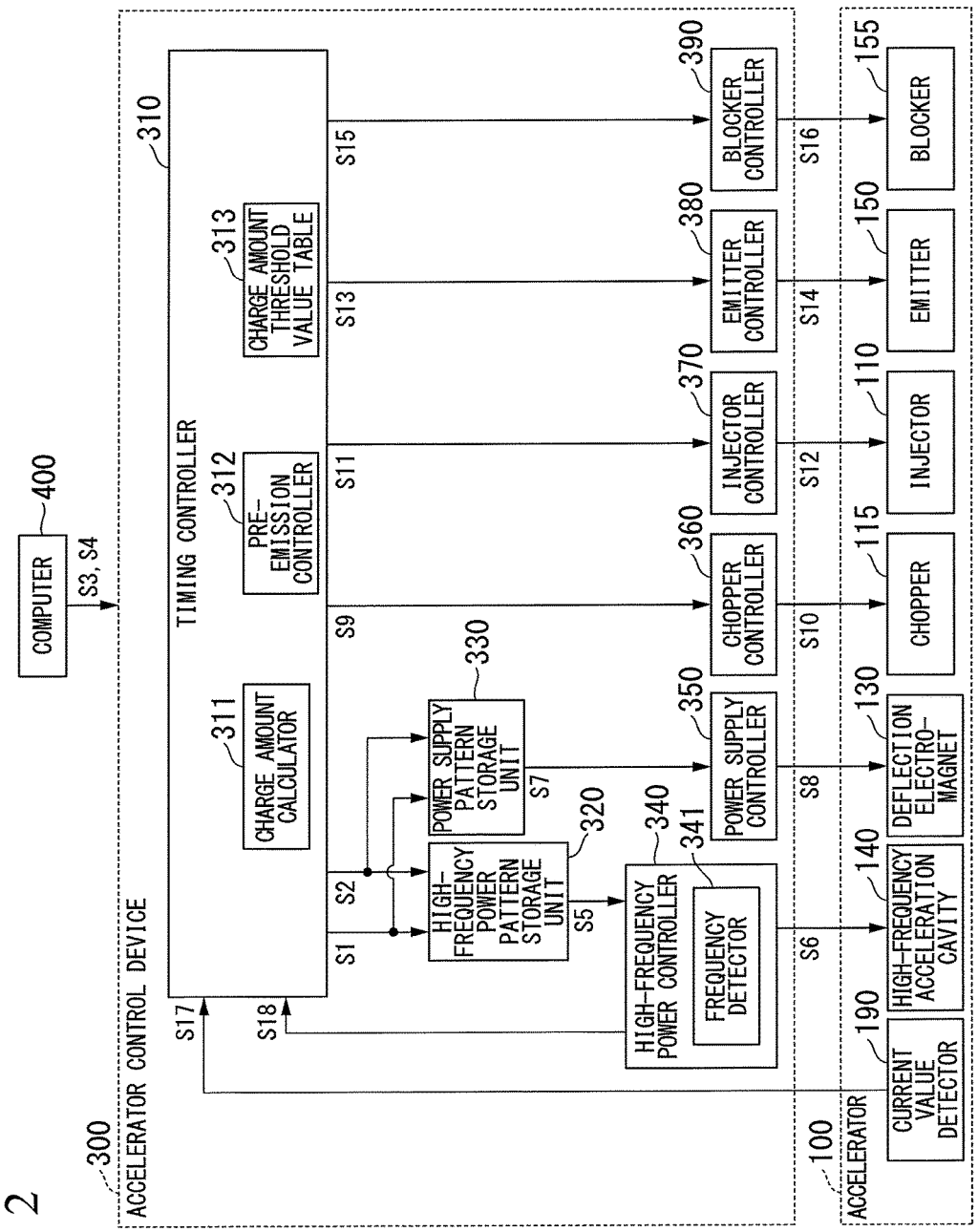
FIG. 2 is a block diagram illustrating a configuration of an accelerator control device 300 according to the first embodiment.

FIG. 2 is a block diagram illustrating a configuration of the accelerator control device 300 according to the first embodiment. The accelerator control device 300 includes a timing controller 310, a high-frequency power pattern storage unit 320, a power supply pattern storage unit 330, a high-frequency power controller 340, a power supply controller 350, a chopper controller 360, an injector controller 370, an emitter controller 380, and a blocker controller 390.

The timing controller 310, the high-frequency power controller 340, the power supply controller 350, the chopper controller 360, the injector controller 370, the emitter controller 380, and the blocker controller 390 are realized by hardware. Examples of such hardware include a field-programmable gate array (FPGA), a large scale integration (LSI), and an application specific integrated circuit (ASIC).

It should be noted that the accelerator control device 300 may include a processor such as a central processing unit (CPU), and a program memory that stores a program to be executed by the processor. In this case, the timing controller 310, the high-frequency power controller 340, the power supply controller 350, the chopper controller 360, the injector controller 370, the emitter controller 380, and the blocker controller 390 may be realized by the processor executing the program stored in the program memory.

The timing controller 310 controls a timing at which the charged particle beam is incident on the accelerator 100 and controls a timing at which the charged particle beam is emitted from the accelerator 100.

As illustrated in FIG. 2, the timing controller 310 outputs a beam incidence signal S11 to the injector controller 370 when the charged particle beam is incident on the circulating trajectory in the accelerator 100. The injector controller 370 supplies incidence power S12 to the injector 110 provided in the accelerator 100 according to the beam incidence signal S11 input from the timing controller 310. When the incidence power S12 is supplied from the injector controller 370, the injector 110 causes the charged particle beam to be incident on the circulating trajectory in the accelerator 100.

Further, when the charged particle beam is emitted from the circulating trajectory in the accelerator 100, the timing controller 310 outputs a beam emission signal S13 to the emitter controller 380. The emitter controller 380 supplies output power S14 to the emitter 150 provided in the accelerator 100 according to the beam emission signal S13 input from the timing controller 310. When the emission power S14 is supplied from the emitter controller 380, the emitter 150 emits the charged particle beam from the circulating trajectory in the accelerator 100 toward the irradiation device 200.

The timing controller 310 controls an operation timing of the blocker 155 that blocks the charged particle beam and controls an operation timing of the chopper 115 for adjusting the amount of the charged particle beam that is incident on the accelerator 100.

As illustrated in FIG. 2, the timing controller 310 outputs a chopper pulse signal S9 to the chopper controller 360 when the amount of the charged particle beam incident from the injector 110 is adjusted. While the chopper pulse signal S9 input from the timing controller 310 is ON, the chopper controller 360 supplies chopper power S10 to the chopper 115 provided in the accelerator 100. When the chopper power S10 is supplied from the chopper controller 360, the chopper 115 passes the charged particle beam incident from the injector 110. On the other hand, when the chopper power S10 is not supplied from the chopper controller 360, the chopper 115 blocks the charged particle beam incident from the injector 110.

It should be noted that the chopper controller 360 supplies the chopper power S10 to the chopper 115 while the chopper pulse signal S9 is ON and does not supply the chopper power S10 to the chopper 115 while the chopper pulse signal S9 is OFF, but the present invention is not limited thereto. For example, the chopper controller 360 may not supply the chopper power S10 to the chopper 115 while the chopper pulse signal S9 is ON but may supply the chopper power S10 to the chopper 115 while the chopper pulse signal S9 is OFF.

Further, when the charged particle beam emitted from the emitter 150 is blocked, the timing controller 310 outputs a blocker driving signal S15 to the blocker controller 390. While the blocker driving signal S15 input from the timing controller 310 is ON, the blocker controller 390 supplies blocker power S16 to the blocker 155. When the blocker power S16 is supplied from the blocker controller 390, the blocker 155 blocks the charged particle beam emitted from the emitter 150. On the other hand, when the blocker power S16 is not supplied from the blocker controller 390, the blocker 155 passes the charged particle beam emitted from the emitter 150.

It should be noted that the blocker controller 390 supplies the blocker power S16 to the blocker 155 while the blocker driving signal S15 is ON, and the blocker controller 390 does not supply the blocker power S16 to the blocker 155 while the blocker driving signal S15 is OFF, but the present invention is not limited thereto. For example, the blocker controller 390 may not supply the blocker driving signal S15 to the blocker 155 while the blocker driving signal S15 is ON, and the blocker controller 390 may supply the blocker driving signal S15 to the blocker 155 while the blocker driving signal S15 is OFF.

A computer 400 is connected to the accelerator control device 300 over a network. When an operator inputs a high-frequency power pattern S3 and a power supply pattern S4 to the computer 400, the computer 400 transmits the input high-frequency power pattern S3 and the input power supply pattern S4 to the accelerator control device 300. When the accelerator control device 300 receives the high-frequency power pattern S3 and the power supply pattern S4 from the computer 400, the accelerator control device 300 stores the received high-frequency power pattern S3 in the high-frequency power pattern storage unit 320 and also stores the received power supply pattern S4 in the power supply pattern storage unit 330. It should be noted that the computer 400 can also set setting values necessary for an operation logic of the emitter controller 380 and setting values necessary for an operation logic of the timing controller 310.

Here, the high-frequency power pattern S3 is data indicating a power command pattern for controlling power supplied to a plurality of electrodes provided in the high-frequency acceleration cavity 140. Specifically, the high-frequency power pattern S3 includes a set of voltage command values for instructing amplitudes of voltages applied to the plurality of electrodes provided in the high-frequency acceleration cavity 140, and a set of frequency command values for instructing frequencies of the voltages applied to the plurality of electrodes, which are executed (output) in a specific order (read as a voltage command value S5).

Further, the power supply pattern S4 is data indicating a current command pattern for controlling currents to be supplied to the plurality of deflection electromagnets 130a to 130d provided in the accelerator 100. That is, the power supply pattern S4 is a set of current command values for instructing the currents to be supplied to the plurality of deflection electromagnets 130a to 130d provided in the accelerator 100, which are executed (output) in a specific order (read as a current command value S7).

The timing controller 310 outputs a reset signal S1 and a clock signal S2 to the high-frequency power pattern storage unit 320. The reset signal S1 is a signal for resetting so that the current command value S5 is generated from the first data of the high-frequency power pattern S3 (read from the first data). The clock signal S2 is a synchronization signal that is used when updating is performed so that the voltage command value S5 is generated from the next data of the high-frequency power pattern S3 (read from the next data).

Further, the timing controller 310 also outputs the reset signal S1 and the clock signal S2 to the power supply pattern storage unit 330. The reset signal S1 is also a signal for resetting so that the current command value S7 is generated from the first data of the power supply pattern S4 (read from the first data). The clock signal S2 is also a synchronization signal that is used when updating is performed so that the current command value S7 is generated from the next data of the power supply pattern S4 (read from the next data).

Figure 3:
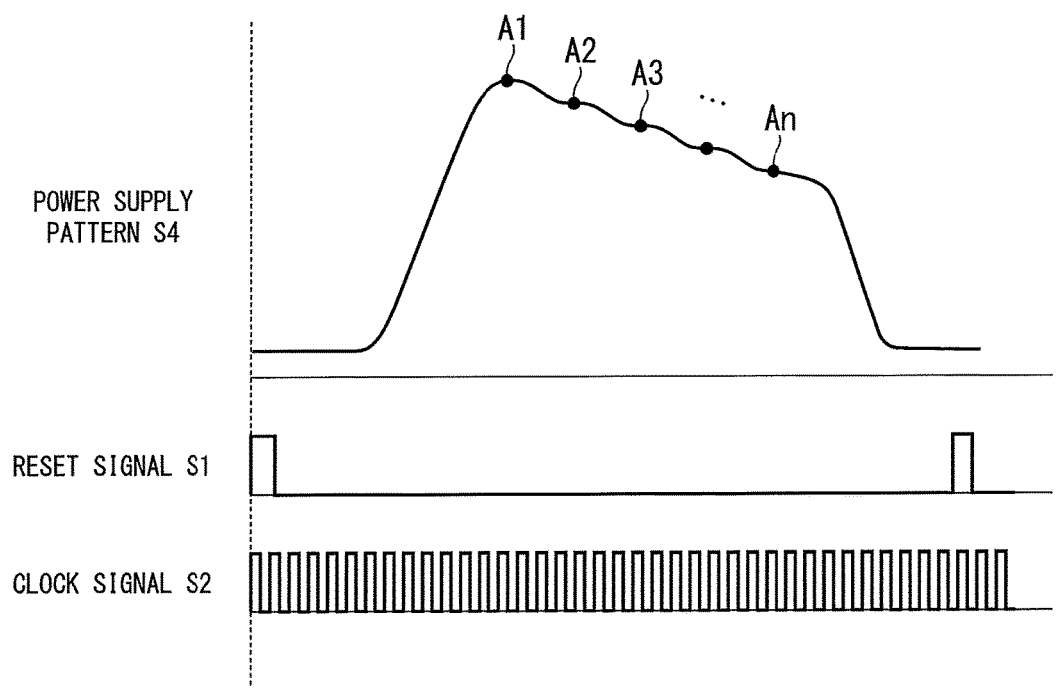
FIG. 3 is a diagram illustrating an example of a power supply pattern S4 according to the first embodiment.

FIG. 3 is a diagram illustrating an example of the power supply pattern S4 according to the first embodiment. In the power supply pattern S4 illustrated in FIG. 3, a horizontal axis indicates time and a vertical axis indicates the current command value for controlling the current supplied from the power supply controller 350 to the deflection electromagnets 130a to 130d. That is, the power supply pattern S4 illustrated in FIG. 3 is read as the current command value S7 from the leftmost current command value (an initial current command value) in FIG. 3. Further, each time the clock signal S2 is input, the next (right adjacent) current command value is sequentially read as the current command value S7. It should be noted that it is possible to increase the current supplied to the deflection electromagnets 130a to 130d when the current command value increases, and it is possible to decrease the current supplied to the deflection electromagnets 130a to 130d when the current command value decreases.

As will be described in detail below, the power supply pattern S4 illustrated in FIG. 3 is a pattern in which the current command value increases to a current command value A1, and then decreases to a current command value A2, a current command value A3, . . . , a current command value An. Here, when the reset signal S1 is input to the power supply pattern storage unit 330, the current command values are forcibly executed in order from the first current command value (a leftmost current command value in FIG. 3) of the power supply pattern S4.

Specifically, the power supply controller 350 counts the number of inputs of the clock signal S2 and reads the current command value S7 corresponding to a count value from the power supply pattern storage unit 330. The power supply controller 350 supplies a current S8 corresponding to the current command value S7 read from the power supply pattern storage unit 330 to the deflection electromagnets 130a to 130d. The power supply controller 350 repeats this operation each time the clock signal S2 is input from the timing controller 310.

The power supply pattern S4 near a timing at which the reset signal S1 is output indicates a current command value corresponding to energy of an incidence level of the charged particle beam. In a case in which the timing controller 310 outputs the beam incidence signal S11 to the injector controller 370 when the current command value is output to the power supply controller 350, the injector controller 370 supplies the incidence power S12 to the injector 110. When the incidence power S12 is supplied to the injector 110, the charged particle beam is output from an ion source (not illustrated), and the injector 110 accelerates the charged particle beam to incidence energy.

Further, the timing controller 310 outputs the chopper pulse signal S9 to the chopper controller 360 at a timing slightly delayed from the beam incidence signal S11. While the chopper pulse signal S9 input from the timing controller 310 is ON, the chopper controller 360 supplies the chopper power S10 to the chopper 115 provided in the accelerator 100. When the chopper power S10 is supplied from the chopper controller 360, the chopper 115 passes the charged particle beam incident from the injector 110.

The charged particle beam that has passed through the chopper 115 is incident on the circulating trajectory of the accelerator 100. Thereafter, acceleration energy is given to the charged particle beam according to the current command value S7 output from the power supply pattern storage unit 330 and the voltage command value S5 output from the high-frequency power pattern storage unit 320. Accordingly, the charged particle beam circulates in the accelerator 100 and accelerates.

The same control is performed on the current given to the quadrupole electromagnets 120a to 120h provided in the accelerator 100 or a current value given to other electromagnets (not illustrated). Normally, resetting, incidence, acceleration, and deceleration are repeated according to the current command value S7 output from the power supply pattern storage unit 330 and the voltage command value S5 output from the high-frequency power pattern storage unit 320.

The current command value S7 does not directly indicate a magnitude of the energy of the charged particle beam. However, the current command value S7 is a value that is uniquely determined on the basis of the energy (speed) of the charged particle beam. When the energy of the charged particle beam is high, the current supplied to the deflection electromagnets 130a to 130d is required to be increased. Therefore, the current command value S7 illustrated in FIG. 2 can also be interpreted as the magnitude of the energy of the charged particle beam.

It should be noted that the high-frequency power controller 340 similarly counts the number of inputs of the clock signal S2 and reads the voltage command value S5 corresponding to a count value from the high-frequency power pattern storage unit 320. The high-frequency power controller 340 applies a voltage S6 according to the voltage command value S5 read from the high-frequency power pattern storage unit 320 to the plurality of electrodes provided in the high-frequency acceleration cavity 140. The high-frequency power controller 340 repeats this operation each time the clock signal S2 is input from the timing controller 310.

The current value detector 190 provided in the accelerator 100 detects the current value S17 of the charged particle beam circulating in the accelerator 100 and transmits the detected current value S17 to the accelerator control device 300. The current value S17 transmitted from the current value detector 190 is input to the timing controller 310.

On the other hand, the high-frequency power controller 340 includes a frequency detector 341. The frequency detector 341 detects a frequency S18 at which the charged particle beam circulates in the accelerator 100. For example, the frequency detector 341 detects the frequency S18 at which the charged particle beam circulates in the accelerator 100 on the basis of the frequency of the voltage applied from the high-frequency power controller 340 to the high-frequency acceleration cavity 140. The frequency detector 341 outputs the detected frequency S18 to the timing controller 310.

The timing controller 310 includes a charge amount calculator 311, a pre-emission controller 312, and a charge amount threshold value table 313 (first table). The charge amount calculator 311 calculates the amount of charge of the charged particle beam by dividing the current value S17 detected by the current value detector 190 by the frequency S18 detected by the frequency detector 341.

A phenomenon called beam spikes in which intensity of the charged particle beam exceeds a target value may occur immediately after the charged particle beam accelerated to a certain energy by the accelerator 100 is emitted. Therefore, the pre-emission controller 312 performs pre-emission in order to prevent occurrence of the beam spikes. The "pre-emission" is an operation of emitting the charged particle beam from the circulating trajectory in the accelerator 100 toward the irradiation device 200 in a state in which the blocker 155 is closed.

Figure 4:
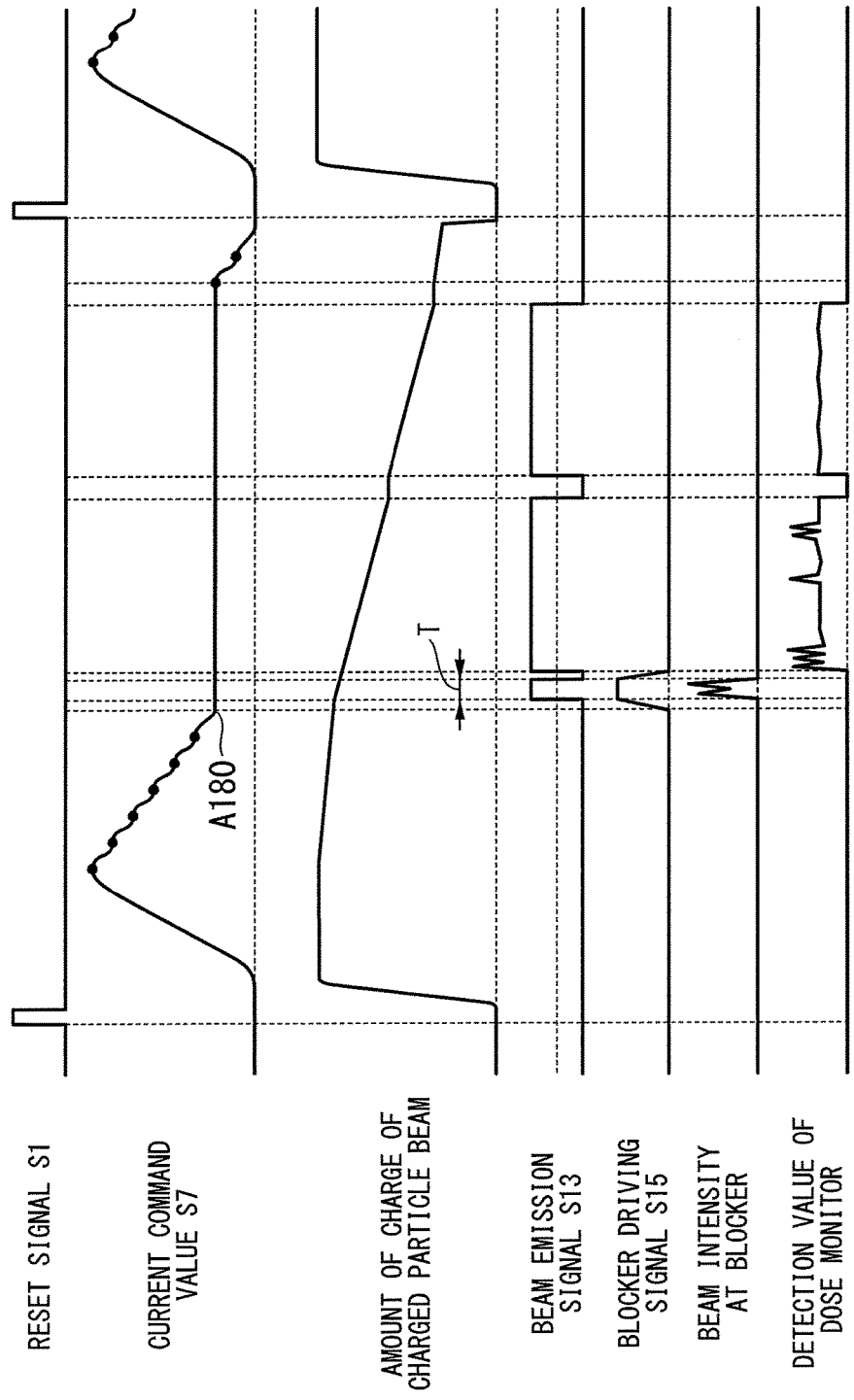
FIG. 4 is a timing chart illustrating an example of control of the blocker 155 when beam spikes occur.

FIG. 4 is a timing chart illustrating an example of control of the blocker 155 when beam spikes occur. For example, in a case in which the charged particle beam is emitted when the current command value S7 is A180, the timing controller 310 stops the clock signal S2 at a timing when the current command value S7 reaches A180. Accordingly, the current supplied to the deflection electromagnets 130a to 130d can be kept constant, such that the energy of the charged particle beam can be kept constant.

After making the energy of the charged particle beam constant, the timing controller 310 outputs the blocker driving signal S15 for closing the blocker 155 to the blocker controller 390. While the blocker driving signal S15 is ON, the blocker controller 390 supplies the blocker power S16 to the blocker 155. When the blocker power S16 is supplied to the blocker 155, the blocker 155 blocks a path of the charged particle beam from the emitter 150 to the irradiation device 200.

After the blocker 155 is closed, the timing controller 310 outputs the beam emission signal S13 for emitting the charged particle beam from the circulating trajectory in the accelerator 100 to the emitter controller 380 until a predetermined time T elapses. The emitter controller 380 supplies the output power S14 to the emitter 150 according to the beam emission signal S13. When the emission power S14 is supplied to the emitter 150, the emitter 150 emits the charged particle beam from the circulating trajectory in the accelerator 100 toward the irradiation device 200.

However, since the blocker 155 is closed, the charged particle beam emitted toward the irradiation device 200 is blocked by the blocker 155. Thus, by performing the pre-emission, it is possible to prevent the charged particle beam in which the beam spikes have occurred from reaching the irradiation device 200. After the pre-emission is performed until the predetermined time T elapses, the timing controller 310 stops outputting the beam emission signal S13. Accordingly, the emitter 150 stops emitting the charged particle beam.

After the emission of the charged particle beam is stopped, the timing controller 310 stops outputting the blocker driving signal S15. Accordingly, the blocker 155 shifts from a closed state to an open state, and a path of the charged particle beam from the emitter 150 to the irradiation device 200 is released. Thereafter, the timing controller 310 outputs the beam emission signal S13 to the emitter controller 380 in order to perform main emission and causes the charged particle beam to be emitted from the emitter 150 to the irradiation device 200.

However, when the energy of the charged particle beam is low (for example, lower than 140 [MeV]) and the amount of charge of the charged particle beam is large (in other words, the number of charged particle beams circulating around the accelerator 100 is large), the beam spikes may occur even when pre-emission for blocking the charged particle beam is performed until the predetermined dine T elapses. In this case, as illustrated in FIG. 4, the dose monitor 210 of the irradiation device 200 detects the occurrence of the beam spikes in which intensity of the charged particle beam exceeds the target value. Therefore, the pre-emission controller 312 needs to control a time to continue the pre-emission in order to prevent the occurrence of the beam spikes.

FIG. 5 is a timing chart illustrating an example of control of the blocker 155 according to the first embodiment. In FIG.

5, a threshold value TH180 is a threshold value of the amount of charge of the charged particle beam in a case in which a current instruction value S7 is A180. The pre-emission controller 312 continues the pre-emission until the amount of charge of the charged particle beam becomes smaller than the threshold value TH180 (until a time Ta elapses). Accordingly, it is possible to prevent the beam spikes from occurring even in a case in which the charged particle beam with low energy is emitted. Hereinafter, the pre-emission control will be described in detail.

As described above, the charge amount calculator 311 calculates the amount of charge of the charged particle beam by dividing the current value S17 detected by the current value detector 190 by the frequency S18 detected by the frequency detector 341. Specifically, the charge amount calculator 311 calculates the amount of charge of the charged particle beam on the basis of Equation (1) below.

$$\text{Amount of charge of charged particle beam } [C] = \text{current value } [A]/\text{frequency } [Hz] \quad (1)$$

The timing controller 310 holds the charge amount threshold value table 313 in which the energy of the charged particle beam is associated with the threshold value of the amount of charge (beam charge amount) of the charged particle beam. For example, the charge amount threshold value table 313 is a table that is stored in a memory provided in the accelerator control device 300.

FIG. 6 is a diagram illustrating an example of the charge amount threshold value table 313 according to the first embodiment. The charge amount threshold value table 313 is a table in which the energy number is associated with the threshold value of the beam charge amount. Specifically, threshold values 100 [nC] to 1 [nC] are associated with energy numbers 1 to 200, respectively. It should be noted that energy number 1 is 430 [MeV], . . . , and energy number 200 is 50 [MeV]. The charge amount threshold value table 313 is set such that the threshold value associated with the energy becomes smaller as the energy of the charged particle beam is lowered.

The pre-emission controller 312 of the timing controller 310 acquires a threshold value corresponding to the energy of the charged particle beam circulating in the accelerator 100 from the charge amount threshold value table 313. The pre-emission controller 312 controls the operation timing of the blocker 155 on the basis of a comparison between the amount of charge calculated by the charge amount calculator 311 and the threshold value acquired from the charge amount threshold value table 313.

For example, when the amount of charge calculated by the charge amount calculator 311 is equal to or greater than the threshold value acquired from the charge amount threshold value table 313, the timing controller 310 controls the blocker 155 such that the charged particle beam is blocked. On the other hand, when the amount of charge calculated by the charge amount calculator 311 is smaller than the threshold value acquired from the charge amount threshold value table 313, the timing controller 310 controls the blocker 155 such that the charged particle beam is passed.

Specifically, when the charged particle beam is emitted with energy corresponding to A180, the pre-emission controller 312 acquires the threshold value TH180 corresponding to the energy of A180 from the charge amount threshold value table 313. When the amount of charge calculated by the charge amount calculator 311 is equal to or greater than the threshold value TH180, the pre-emission controller 312 closes the blocker 155 and performs pre-emission. On the other hand, according to the amount of charge calculated by the charge amount calculator 311 becoming smaller than the threshold value TH180, the pre-emission controller 312 ends the pre-emission and opens the blocker 155. After the pre-emission is completed, the timing controller 310 performs main emission for emitting the charged particle beam to the irradiation device 200.

As described above, the pre-emission controller 312 continues the pre-emission until the amount of charge of the charged particle beam becomes smaller than the threshold value. Accordingly, it is possible to prevent the beam spikes from occurring even in a case in which the charged particle beam with low energy is emitted. In the first embodiment, the occurrence of the beam spikes is not detected by the dose monitor 210 of the irradiation device 200, as illustrated in FIG. 5.

The threshold value of the amount of beam charge illustrated in FIG. 6 is adjusted in a beam adjustment test in advance. At the time of treatment, pre-emission is performed on the basis of the adjusted threshold value. For example, it is assumed that a maximum value of the amount of charge of the charged particle beam circulating around the accelerator 100 is 10 [nC]. In this case, a value much larger than 10 [nC] (for example, 100 [nC]) may be set as a threshold value corresponding to high energy, as illustrated in FIG. 6. Accordingly, when a high-energy charged particle beam is emitted, the amount of charge of the charged particle beam in the accelerator 100 is already below the threshold value, and therefore, the pre-emission controller 312 does not perform pre-emission time extension. Therefore, the pre-emission controller 312 can emit the charged particle beam after performing the pre-emission until the predetermined time T elapses.

FIG. 7 is a diagram illustrating another example of the charge amount threshold value table 313 according to the first embodiment. As illustrated in FIG. 7, a boundary energy number may be set in the charge amount threshold value table 313. Further, a beam charge amount threshold value 1 from energy number 1 to a boundary energy number and a beam charge amount threshold value 2 from the boundary energy number +1 to energy number 200 (a maximum value) may be set in the charge amount threshold value table 313.

Specifically, in the example illustrated in FIG. 7, a beam charge amount threshold value (20 [nC]) is associated with energy numbers 1 to 180 and a beam charge amount threshold value (1 [nC]) is associated with energy numbers 181 to 200.

FIG. 8 is a diagram illustrating another example of the charge amount threshold value table 313 according to the first embodiment. As illustrated in FIG. 8, boundary energy number 1 and boundary energy number 2 may be set in the charge amount threshold value table 313. Further, in the charge amount threshold value table 313, a beam charge amount threshold value 1 from energy number 1 to boundary energy number 1, a beam charge amount threshold value 2 from boundary energy number 1+1 to boundary energy number 2, and a beam charge amount threshold value 3 from boundary energy number 2+1 to energy number 200 (a maximum value) may be set.

Specifically, in the example illustrated in FIG. 8, a beam charge amount threshold value (10 [nC]) is associated with energy numbers 1 to 150, a beam charge amount threshold value (2 [nC]) is associated with energy numbers 151 to 180, and a beam charge amount threshold value (1 [nC]) is associated with energy numbers 181 to 200.

As in the example illustrated in FIG. 7 or 8, the charge amount threshold value table 313 may include boundary energy for delimiting a range of energy, and a threshold value of the amount of charge of the charged particle beam may be associated with each range of energy delimited by the boundary energy. Accordingly, it is possible to reduce the amount of data of the charge amount threshold value table 313.

Figure 9:
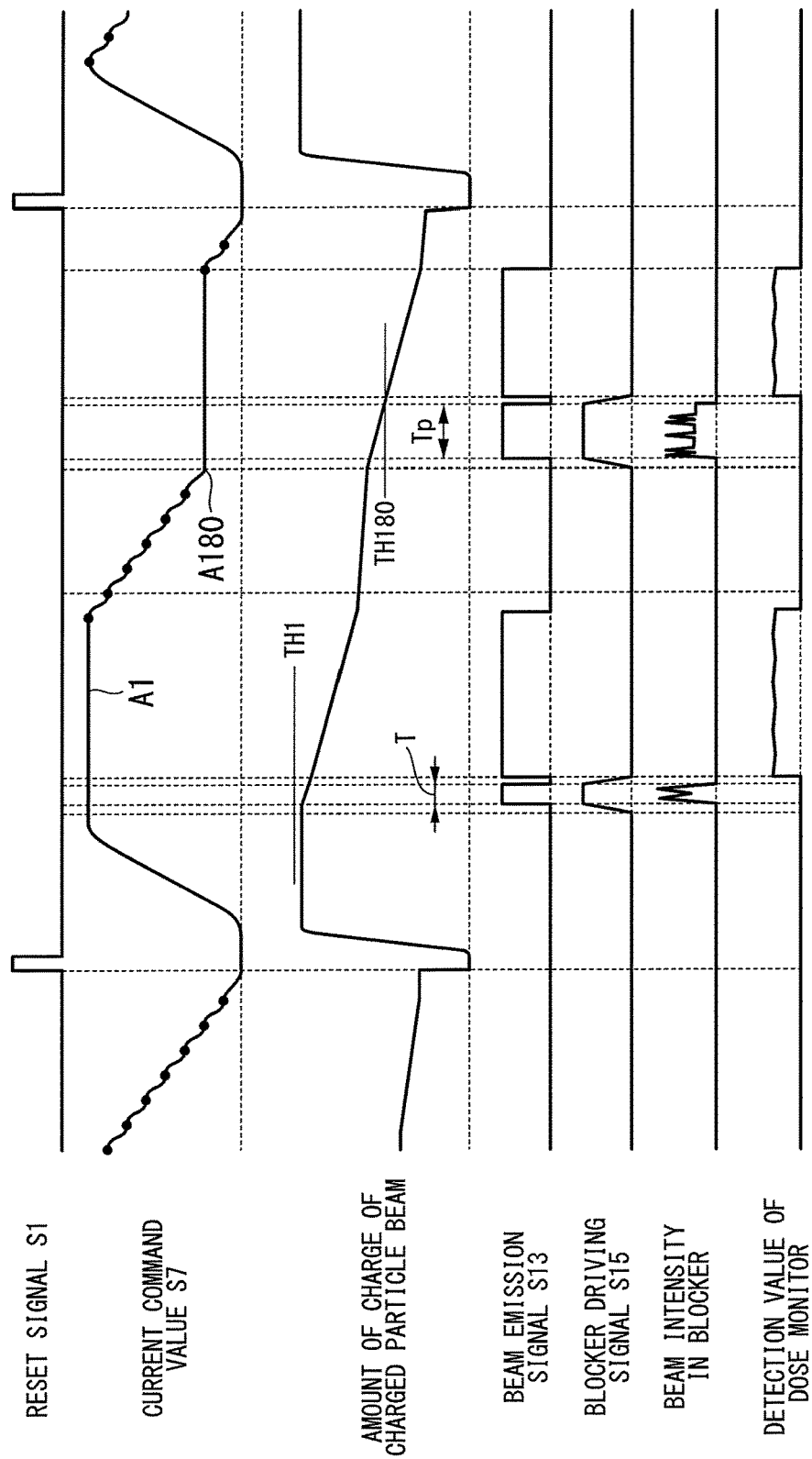
FIG. 9 is a timing chart illustrating another example of the control of the blocker 155 according to the first embodiment.

FIG. 9 is a timing chart illustrating another example of the control of the blocker 155 according to the first embodiment. Specifically, FIG. 9 is a timing chart illustrating the control of emitting the charged particle beam of a first energy stage (A1) and the charged particle beam of a 180th energy stage (A180).

The charged particle beam incident on the accelerator 100 by the injector 110 is accelerated by the accelerator 100. When the clock signal S2 reaches a count value corresponding to the first energy stage (A1), the timing controller 310 stops the clock signal S2. Accordingly, the energy of the charged particle beam is held at a constant value (A1). In this case, since the amount of charge of the charged particle beam is smaller than the threshold value TH1, pre-emission is performed until the predetermined time T elapses. After the pre-emission is completed, main emission of the first energy stage (A1) is performed.

When the main emission of the first energy stage (A1) is completed, the timing controller 310 resumes the supply of the clock signal S2. When the clock signal S2 reaches a count value corresponding to the 180th energy stage (A180), the timing controller 310 stops the clock signal S2. Accordingly, the energy of the charged particle beam is held at a constant value (A180). In this case, since the amount of charge of the charged particle beam is greater than the threshold value TH180, pre-emission is performed until a predetermined time Tp elapses (until the amount of charge of the charged particle beam becomes smaller than the threshold value TH180). After the pre-emission is completed, the main emission of the 180th energy stage (A180) is performed.

Accordingly, it is possible to prevent the beam spikes from occurring in any main emissions even in a case in which a plurality of main emissions with different energies are performed.

As described above, in the first embodiment, the timing controller 310 controls the operation timing of the blocker 155 which blocks the charged particle beam emitted from the accelerator 100 on the basis of the current value of the charged particle beam circulating in the accelerator 100. Specifically, the timing controller 310 calculates the amount of charge of the charged particle beam on the basis of the current value detected by the current value detector 190, and controls an operation timing of the blocker 155 on the basis of the calculated amount of charge of the charged particle beam. Accordingly, it is possible to prevent beam spikes from occurring even in a case in which the charged particle beam with low energy is emitted.

Second Embodiment

In the first embodiment, the timing controller 310 controls the operation timing of the blocker 155 that blocks the charged particle beam emitted from the accelerator 100. On the other hand, in a second embodiment, the timing controller 310 controls the pulse width of the chopper pulse signal for driving the chopper 115, in addition to controlling the operation timing of the blocker 155. Hereinafter, the second embodiment will be described in detail.

Figure 10:
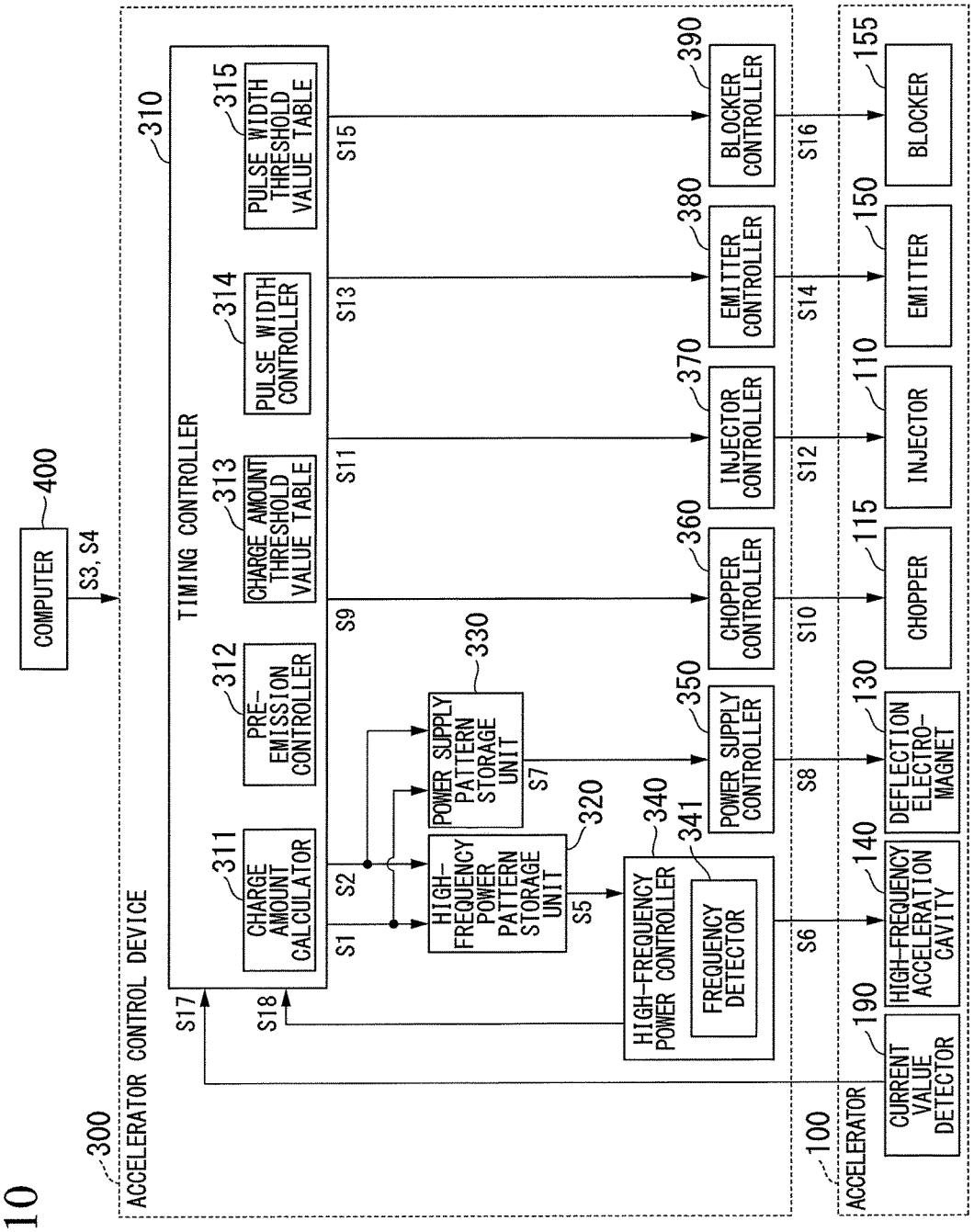
FIG. 10 is a block diagram illustrating a configuration of an accelerator control device 300 according to a second embodiment.

FIG. 10 is a block diagram illustrating a configuration of the accelerator control device 300 according to a second embodiment. In FIG. 10, portions corresponding to those in FIG. 2 are denoted by the same reference numerals, and description thereof is omitted.

The timing controller 310 includes a pulse width controller 314 and a pulse width threshold value table 315 (a second table) in addition to the charge amount calculator 311, the pre-emission controller 312, and the charge amount threshold value table 313. The pulse width threshold value table 315 is a table that is stored in the memory provided in the accelerator control device 300.

The pulse width controller 314 performs pulse width control of the chopper pulse signal S9 in order to prevent the beam spikes from occurring. The pulse width controller 314 adjusts the amount of the charged particle beam incident on the circulating trajectory in the accelerator 100 by performing the pulse width control.

Figure 11:
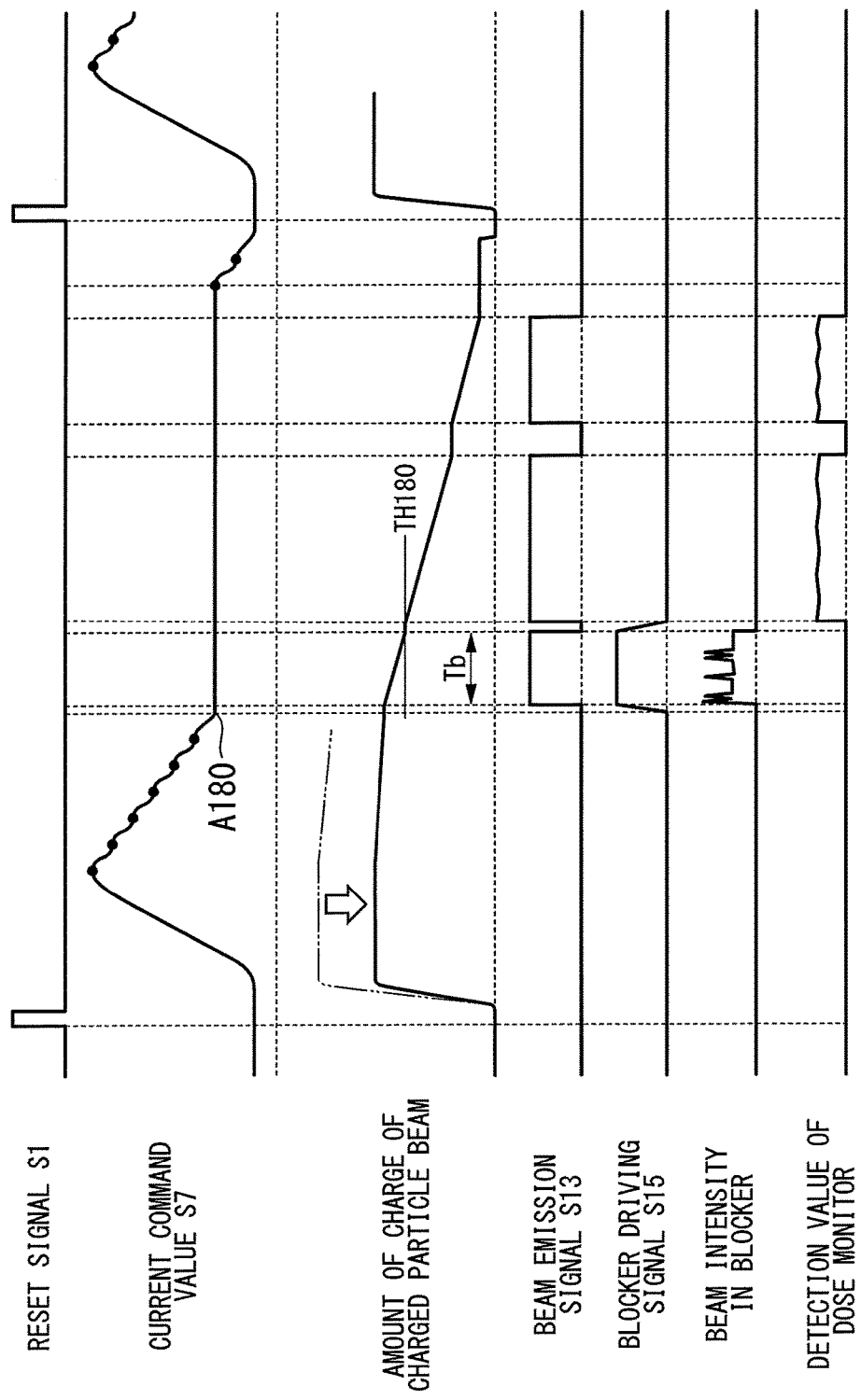
FIG. 11 is a timing chart illustrating an example of control of a blocker 155 and a chopper 115 according to the second embodiment.

FIG. 11 is a timing chart illustrating an example of control of the blocker 155 and the chopper 115 according to the second embodiment. In FIG. 11, portions corresponding to the respective portions in FIG. 5 are denoted by the same reference numerals, and description thereof is omitted. FIG. 11 is a timing chart in a case in which the charged particle beam is emitted with low energy (A180).

In a case in which the charged particle beam is emitted with low energy (A180), it is easy for the beam spikes to occur, and therefore, it is preferable to reduce the amount of charge of the charged particle beam in advance. Therefore, the chopper controller 360 controls the chopper 115 on the basis of the energy of the charged particle beam when the charged particle beam is emitted from the accelerator 100, thereby adjusting the amount of charged particle beam incident on the circulating trajectory in the accelerator 100.

In the example illustrated in FIG. 5 described above, since the amount of the charged particle beam incident on the circulating trajectory in the accelerator 100 is large, the pre-emission takes a long time Ta. On the other hand, in the example illustrated in FIG. 11, the pulse width controller 314 controls the pulse width of the chopper pulse signal S9 to be output to the chopper controller 360, such that the amount of charged particle beam incident on the circulating trajectory in the accelerator 100 is reduced. Accordingly, the amount of charge of the charged particle beam becomes small, and therefore, the pre-emission can be ended in a short time Tb. In addition, by shortening the time required for pre-emission, it is possible to improve treatment efficiency and reduce a burden on the patient.

FIG. 12 is a diagram illustrating an example of the pulse width threshold value table 315 according to the second embodiment. The pulse width threshold value table 315 is a table in which the energy of the charged particle beam and the pulse width of the chopper pulse signal for driving the chopper 115 are associated with each other. Specifically, chopper pulse widths of 40 [μs] to 10 [μs] are associated with energy numbers 1 to 200, respectively. It should be noted that energy number 1 is 430 [MeV], . . . , and energy number 200 is 50 [MeV]. The pulse width threshold value table 315 is set such that the pulse width associated with the energy becomes smaller as the energy of the charged particle beam is lower.

The pulse width controller 314 acquires the pulse width corresponding to the energy of the charged particle beam when the charged particle beam is emitted from the accelerator 100 from the pulse width threshold value table 315. The chopper controller 360 controls the operation timing of the chopper 115 on the basis of the pulse width acquired by the pulse width controller 314.

For example, the chopper controller 360 controls a time for supplying the chopper power S10 to the chopper 115 on the basis of the pulse width acquired by the pulse width controller 314. Specifically, when the chopper pulse width is 10 [μs], the chopper controller 360 sets a supply time of the chopper power S10 to 10 μs.

As described above, the pulse width controller 314 controls the chopper pulse width for driving the chopper 115 on the basis of the energy of the charged particle beam when the charged particle beam is emitted from the accelerator 100. Specifically, when the energy of the charged particle beam when the charged particle beam is emitted from the accelerator 100 is low, the pulse width controller 314 reduces the amount of charged particle beam incident on the circulating trajectory in the accelerator 100 by decreasing the chopper pulse width. Thus, it is possible to shorten the time required for pre-emission.

FIG. 13 is a diagram illustrating another example of the pulse width threshold value table 315 according to the second embodiment. As illustrated in FIG. 13, a boundary energy number may be set in the pulse width threshold value table 315. Also, in the pulse width threshold value table 315, a chopper pulse width 1 from energy number 1 to the boundary energy number and a chopper pulse width 2 from a boundary energy number +1 to energy number 200 (maximum value) may be set.

Specifically, in the example illustrated in FIG. 13, the chopper pulse width (30 μs) is associated with energy numbers 1 to 180, the chopper pulse width (10 μs) is associated with energy numbers 181 to 200.

FIG. 14 is a diagram illustrating another example of the pulse width threshold value table 315 according to the second embodiment. As illustrated in FIG. 14, boundary energy number 1 and boundary energy number 2 may be set in the pulse width threshold value table 315. Further, in the pulse width threshold value table 315, a chopper pulse width 1 from energy number 1 to boundary energy number 1, a chopper pulse width 2 from a boundary energy number 1+1 to boundary energy number 2, and a chopper pulse width 3 from boundary energy number 2+1 to energy number 200 (maximum value) may be set.

Specifically, in the example illustrated in FIG. 14, a chopper pulse width (30 μs) is associated with energy numbers 1 to 100, a chopper pulse width (20 μs) is associated with energy numbers 101 to 180, and a chopper pulse width (10 μs) is associated with energy numbers 181 to 200.

As in the example illustrated in FIG. 13 or FIG. 14, the pulse width threshold value table 315 may include a boundary energy for delimiting the range of energy, and a chopper pulse width may be associated with each range of energy delimited by the boundary energy. Accordingly, it is possible to reduce the amount of data of the pulse width threshold value table 315.

As described above, in the second embodiment, the timing controller 310 acquires the pulse width corresponding to the energy of the charged particle beam when the charged particle beam is emitted from the accelerator 100 from the pulse width threshold value table 315. The chopper controller 360 controls the operation timing of the chopper 115 on the basis of the pulse width acquired by the timing controller 310. Thus, it is possible to prevent the beam spikes from occurring and shorten the time required for pre-emission.

Third Embodiment

The timing controller 310 of the first embodiment and the second embodiment calculates the amount of charge of the charged particle beam on the basis of the current value of the charged particle beam circulating in the accelerator 100 and controls the operation timing of the blocker 155 on the basis of the calculated amount of charge of the charged particle beam. On the other hand, a timing controller 310 according to the third embodiment controls the operation timing of the blocker 155 on the basis of a current value (a beam current) of the charged particle beam circulating in the accelerator 100 without calculating the amount of charge of the charged particle beam. Hereinafter, the third embodiment will be described in detail.

Figure 15:
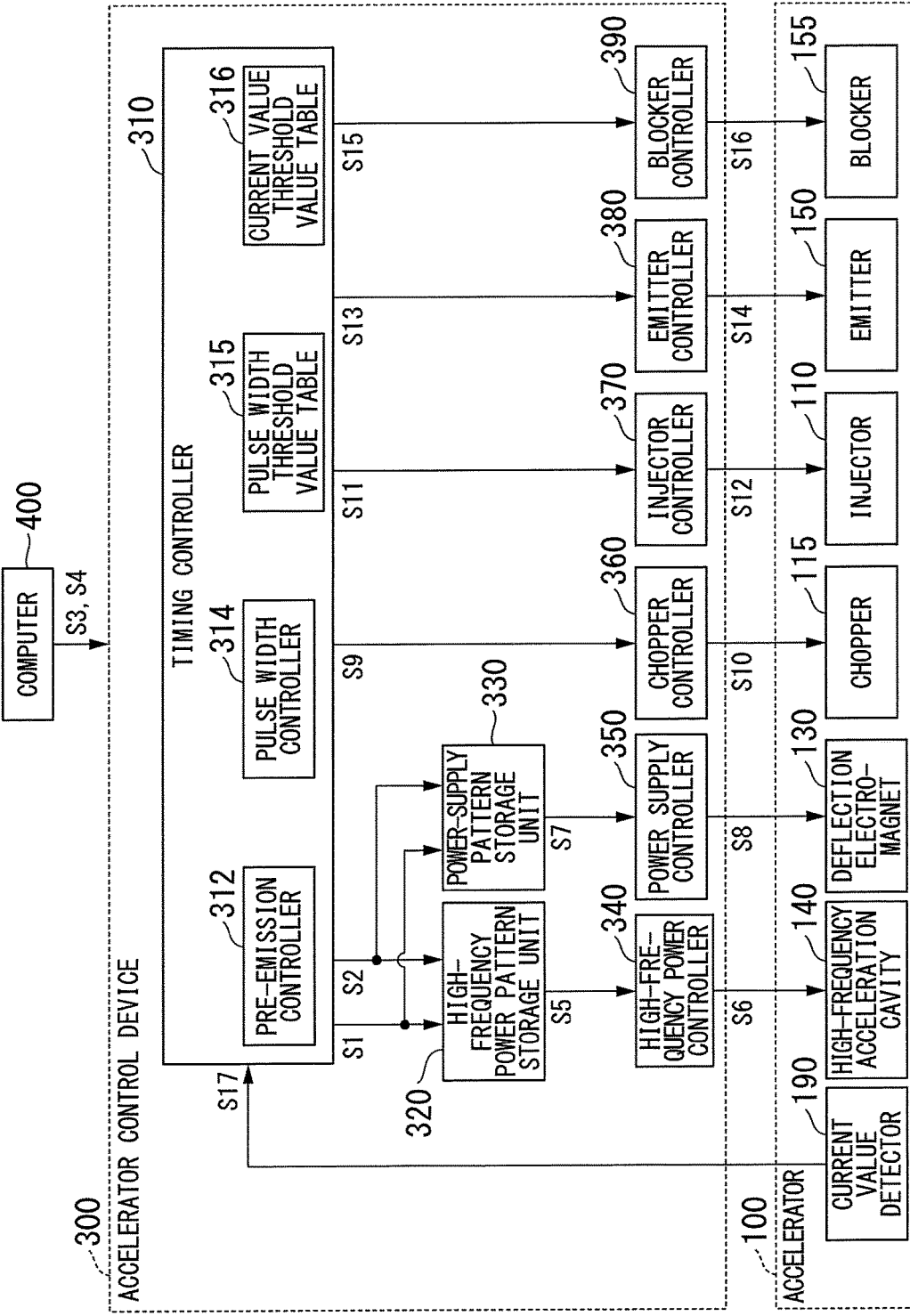
FIG. 15 is a block diagram illustrating a configuration of an accelerator control device 300 according to a third embodiment.

FIG. 15 is a block diagram illustrating a configuration of the accelerator control device 300 according to the third embodiment. In FIG. 15, portions corresponding to the respective portions in FIG. 10 are denoted by the same reference numerals, and description thereof is omitted.

In the third embodiment, since the timing controller 310 does not calculate the amount of charge of the charged particle beam, the timing controller 310 does not include the charge amount calculator 311. Further, the high-frequency power controller 340 does not include the frequency detector 341. On the other hand, the timing controller 310 includes a current value threshold value table 316 (a third table), in addition to the pre-emission controller 312, the pulse width controller 314, and the pulse width threshold value table 315. The current value threshold value table 316 is a table that is stored in the memory provided in the accelerator control device 300.

Figures 16, 17, 18:
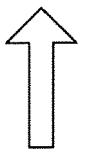
FIG. 16 is a diagram illustrating an example of a current value threshold value table 316 according to the third embodiment.
FIG. 17 is a diagram illustrating another example of the current value threshold value table 316 according to the third embodiment.
FIG. 18 is a diagram illustrating another example of the current value threshold value table 316 according to the third embodiment.

FIG. 16 is a diagram illustrating an example of the current value threshold value table 316 according to the third embodiment. The current value threshold value table 316 is a table in which the energy number and the threshold value of the beam current are associated with each other. Specifically, threshold values 50 [mA] to 0.5 [mA] are associated with energy numbers 1 to 200, respectively. It should be noted that energy number 1 is 430 [MeV], . . . , and energy number 200 is 50 [MeV]. The current value threshold value table 316 is set such that the threshold value associated with the energy becomes smaller as the energy of the charged particle beam is lower.

The timing controller 310 acquires a threshold value corresponding to the energy of the charged particle beam circulating in the accelerator 100 from the current value threshold value table 316. Further, the pre-emission controller 312 of the timing controller 310 controls the operation timing of the blocker 155 on the basis of a comparison between the current value of the charged particle beam circulating in the accelerator 100 and the threshold value acquired from the current value threshold value table 316.

For example, when the current value detected by the current value detector 190 is equal to or greater than the threshold value acquired from the current value threshold value table 316, the timing controller 310 controls the blocker 155 such that the charged particle beam is blocked. On the other hand, when the current value detected by the current value detector 190 is smaller than the threshold value acquired from the current value threshold value table 316, the timing controller 310 controls the blocker 155 such that the charged particle beam is passed.

As described above, the pre-emission controller 312 continues pre-emission until the current value of the charged particle beam becomes smaller than the threshold value. Accordingly, it is possible to prevent the beam spikes from occurring. In addition, since the charge amount calculator 311 and the frequency detector 341 are not required, it is possible to reduce costs of the accelerator control device 300.

FIG. 17 is a diagram illustrating another example of the current value threshold value table 316 according to the third embodiment. As illustrated in FIG. 17, the boundary energy number may be set in the current value threshold value table 316. Further, in the current value threshold value table 316, a beam current threshold value 1 from energy number 1 to a boundary energy number and a beam current threshold value 2 from boundary energy number +1 to energy number 200 (a maximum value) may be set.

Specifically, in the example illustrated in FIG. 17, a beam current threshold value (10 [mA]) is associated with energy numbers 1 to 180, and a beam current threshold value (0.5 [mA]) is associated with energy numbers 181 to 200.

FIG. 18 is a diagram illustrating another example of the current value threshold value table 316 according to the third embodiment. As illustrated in FIG. 18, boundary energy number 1 and boundary energy number 2 may be set in the current value threshold value table 316. Further, in the current value threshold value table 316, a beam current threshold value 1 from energy number 1 to boundary energy number 1, a beam current threshold value 2 from boundary energy number 1+1 to boundary energy number 2, and a beam current threshold value 3 from boundary energy number 2+1 to energy number 200 (a maximum value) may be set.

Specifically, in the example illustrated in FIG. 18, the beam current threshold value (5 [mA]) is associated with energy numbers 1 to 150, a beam current threshold value (1 [mA]) is associated with energy numbers 151 to 180, and a beam current threshold value (0.25 [mA]) is associated with energy numbers 181 to 200.

As in the example illustrated in FIG. 17 or 18, the current value threshold value table 316 may include a boundary energy for delimiting a range of energy, and a threshold value of the current value of the charged particle beam may be associated with each range of energy delimited by the boundary energy. Accordingly, it is possible to reduce the amount of data of the current value threshold value table 316.

According to at least one embodiment described above, the accelerator control device 300 includes the high-frequency power controller 340 and the timing controller 310. The high-frequency power controller 340 supplies high-frequency power for accelerating the charged particle beam to the accelerator 100. The timing controller 310 controls the operation timing of the blocker 155 which blocks the charged particle beam emitted from the accelerator 100 on the basis of the current value of the charged particle beam circulating in the accelerator 100. Accordingly, it is possible to prevent the beam spikes from occurring even in a case in which the charged particle beam with low energy is emitted.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An accelerator control device comprising:
   a high-frequency power controller that supplies high frequency power for accelerating a charged particle beam to an accelerator; and
   a timing controller that controls an operation timing of a blocker that blocks the charged particle beam emitted from the accelerator on the basis of a current value of the charged particle beam circulating in the accelerator.

2. The accelerator control device according to claim 1, further comprising:
   a frequency detector that detects a frequency at which the charged particle beam circulates in the accelerator; and
   a charge amount calculator that calculates the amount of charge of the charged particle beam by dividing the current value of the charged particle beam circulating in the accelerator by the frequency detected by the frequency detector,
   wherein the timing controller controls an operation timing of the blocker on the basis of the amount of charge calculated by the charge amount calculator.

3. The accelerator control device according to claim 2, wherein the timing controller
   holds a first table in which energy of the charged particle beam is associated with a threshold value of the amount of charge of the charged particle beam,
   acquires the threshold value corresponding to the energy of the charged particle beam circulating in the accelerator from the first table, and
   controls the operation timing of the blocker on the basis of a comparison between the amount of charge calculated by the charge amount calculator and the threshold value acquired from the first table.

4. The accelerator control device according to claim 3, wherein the timing controller
   controls the blocker such that the charged particle beam is blocked when the amount of charge calculated by the charge amount calculator is equal to or greater than the threshold value acquired from the first table, and
   controls the blocker such that the charged particle beam is passed when the amount of charge calculated by the charge amount calculator is smaller than the threshold value acquired from the first table.

5. The accelerator control device according to claim 3, wherein the first table includes boundary energy for delimiting a range of energy, and the threshold value of the amount of charge of the charged particle beam is associated with each range of energy delimited by the boundary energy.

6. The accelerator control device according to claim 3, wherein the first table is set such that the threshold value associated with the energy becomes smaller as the energy of the charged particle beam is lower.

7. The accelerator control device according to claim 1, further comprising:
   a chopper controller that controls a chopper for adjusting the amount of the charged particle beam incident on the accelerator,
   wherein the timing controller
   holds a second table in which the energy of the charged particle beam is associated with a pulse width of a pulse signal for driving the chopper, and
   acquires the pulse width corresponding to the energy of the charged particle beam when the charged particle beam is emitted from the accelerator from the second table, and
   the chopper controller controls an operation timing of the chopper on the basis of the pulse width acquired by the timing controller.

8. The accelerator control device according to claim 7, wherein the second table includes boundary energy for delimiting a range of energy, and the pulse width is associated with each range of energy delimited by the boundary energy.

9. The accelerator control device according to claim 7, wherein the second table is set such that the pulse width associated with the energy becomes smaller as the energy of the charged particle beam is lower.

10. The accelerator control device according to claim 1, wherein the timing controller holds a third table in which the energy of the charged particle beam is associated with a threshold value of the current value of the charged particle beam, acquires the threshold value corresponding to the energy of the charged particle beam circulating in the accelerator from the third table, and controls the operation timing of the blocker on the basis of a comparison between the current value of the charged particle beam circulating in the accelerator and the threshold value acquired from the third table.

11. The accelerator control device according to claim 10, wherein the timing controller controls the blocker such that the charged particle beam is blocked when the current value of the charged particle beam circulating in the accelerator is equal to or greater than the threshold value acquired from the third table, and controls the blocker such that the charged particle beam is passed when the current value of the charged particle beam circulating in the accelerator is smaller than the threshold value acquired from the third table.

12. The accelerator control device according to claim 10, wherein the third table includes boundary energy for delimiting a range of energy, and the threshold value of the current value of the charged particle beam is associated with each range of energy delimited by the boundary energy.

13. The accelerator control device according to claim 10, wherein the third table is set such that the threshold value associated with the energy becomes smaller as the energy of the charged particle beam is lower.

14. An accelerator control method for controlling an accelerator that accelerates a charged particle beam, the accelerator control method comprising:

supplying, by a high-frequency power controller, high frequency power for accelerating the charged particle beam to the accelerator; and controlling, by a timing controller, an operation timing of a blocker that blocks the charged particle beam emitted from the accelerator on the basis of a current value of the charged particle beam circulating in the accelerator.

15. A particle beam therapy device, comprising:

an accelerator that accelerates a charged particle beam;

a high-frequency power controller that supplies high-frequency power for accelerating the charged particle beam to the accelerator;

an emitter that emits the charged particle beam accelerated by the accelerator;

a blocker that blocks the charged particle beam emitted by the emitter;

a current value detector that detects a current value of the charged particle beam circulating in the accelerator; and a timing controller that controls an operation timing of the blocker on the basis of the current value detected by the current value detector.

* * * * *